US00PP10406P

United States Patent [19]

VandenBerg

[11] Patent Number: Plant 10,406

[45] Date of Patent: May 19, 1998

[54] CHRYSANTHEMUM PLANT NAMED 'GOLDEN ALBANY'

[75] Inventor: Cornelis P. VandenBerg, Salinas, Calif.

[73] Assignee: Yoder Brothers, Inc., Barberton, Ohio

[21] Appl. No.: 709,745

[22] Filed: Sep. 9, 1996

[51] Int. Cl.[6] ..... A01H 5/00

[52] U.S. Cl. ..... Plt./78

[58] Field of Search ..... Plt./78

[56] References Cited

U.S. PATENT DOCUMENTS

| | | | |
|---|---|---|---|
| P.P. 9,595 | 6/1996 | Glicenstein | Plt./77 |
| 4,616,099 | 10/1986 | Sparkes | 47/58 |

OTHER PUBLICATIONS

Broertjes, et al., 1980, "A Mutant of a Mutant of a . . . Irradiation of Progressive Radiation–Induced Mutants in a Mutation Breeding Programme with *Chrysanthemum morifolium*", Euphytica, 29:525–530.

Gosling, ed., 1979, "The Chrysanthemum Manual—6th Edition", The National Chrysanthemum Society, London, Essex Telegraph Press, Ltd., pp. 329–336.

Broertjes, et al., 1978, "Application of Mutation Breeding Methods in the Improvement of Vegetatively Propagated Crops", Elsevier Sci. Pub. Co., New York, pp. 162–175.

Searle, et al., 1968, "Chrysanthemums the Year Rround", Blanford Press, London, pp. 27–29, 320–327.

Chan, 1966, "Chrysanthemum and Rose Mutations Induced by X–rays", Am. Soc. Hort. Sci. Proc., pp. 613–620.

Broertjes, 1966, "Mutation Breeding of Chrysanthemums", Euphytica, 15: 156–162.

Dowrick, et al., 1966, "The Induction of Mutations in Chrysanthemum Using X– and Gamma Radiation", Euphytica 15: 204–210.

*Primary Examiner*—Howard J. Locker
*Attorney, Agent, or Firm*—C. A. Whealy

[57] ABSTRACT

A distinct cultivar of Chrysanthemum plant named 'Golden Albany', characterized by its slightly domed capitulum form; decorative-type inflorescences; attractive bright yellow ray florets; numerous inflorescences per plant; uniform flowering in year-round production; and good postproduction longevity.

3 Drawing Sheets

The present invention relates to a new and distinct cultivar of Chrysanthemum plant, botanically known as *Dendranthema grandiflora* and referred to by the cultivar name 'Golden Albany'.

The new cultivar is a product of a mutation induction breeding program conducted by the inventor in Salinas, Calif. The objective of the breeding program is to create new Chrysanthemum cultivars having inflorescences with desirable colors and good form and substance.

The new cultivar originated by exposing 75 unrooted cuttings of the Chrysanthemum cultivar 'Albany' (U.S. Plant Pat. No. 9,595) to an X-ray radiation level of 1,500 rads in September, 1993. Following the radiation treatment, the cuttings were rooted and terminal apices were removed (pinched) three times to promote lateral branch development. After lateral branches from the third pinch reached sufficient size, 346 terminal cuttings were harvested, planted and flowered in a controlled environment in Salinas, Calif. The cultivar 'Golden Albany' was discovered and selected by the inventor as a single flowering plant within this population in March, 1994. The selection of this plant was based on its desirable inflorescence color and good form and substance.

Asexual reproduction of the new cultivar by terminal cuttings taken in a controlled environment in Salinas, Calif., has shown that the unique features of this new Chrysanthemum are stable and reproduced true to type in successive generations.

The cultivar Golden Albany has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Golden Albany'. These characteristics in combination distinguish 'Golden Albany' as a new and distinct cultivar:

1. Slightly domed capitulum form.
2. Decorative-type inflorescences that are about 8 cm in diameter when fully open.
3. Attractive bright yellow ray florets.
4. Numerous inflorescences per plant.
5. Uniform flowering in year-round production.
6. Good postproduction longevity with inflorescences maintaining good substance and color for more than three weeks in an interior environment after one week in cool storage.

The new Chrysanthemum is similar in plant habit to the mutation parent cultivar Albany. However in side-by-side comparisons in Salinas, Calif., under commercial practice, plants of the new Chrysanthemum differ from plants of the cultivar Albany in the following characteristics:

1. Plants of the new Chrysanthemum have ray florets that are bright yellow in color whereas ray florets of plants of 'Albany' are white in color.
2. Plants of the new Chrysanthemum are typically taller than plants of the cultivar 'Albany'.
3. Plants of the new Chrysanthemum flower several days later than plants of the cultivar 'Albany'.

The accompanying colored photographs illustrate the overall appearance of the new cultivar, showing the colors as true as it is reasonably possible to obtain in colored reproductions of this type.

The first photograph comprises a side perspective view of a typical flowering stem of 'Golden Albany' grown as a single stem spray cut chrysanthemum.

The second photograph comprises a top perspective view of inflorescences of the cultivar 'Golden Albany' at three different stages of development: unopened inflorescence, opening inflorescence, and fully opened inflorescence.

The third photograph comprises a top perspective view of the adaxial surface of leaves of the cultivar 'Golden Albany' at three different stages of development showing the differences in size and lobation development.

Floret and foliage colors may appear different from the actual due to light reflectance.

In the following description, color references are made to The Royal Horticultural Society Colour Chart except where general terms of ordinary dictionary significance are used. The following observations and measurements describe plants grown in Salinas, Calif., under commercial practice in a polyethylene-covered greenhouse with night temperatures ranging from 15 to 17C, day temperatures up to 24C, and light levels of 2,500 to 3,000 footcandles. After planting rooted cuttings of the new cultivar, plants received 11 long day/short nights following by short day/long nights until flowering. Measurements and numerical values represent averages for six typical flowering stems.

Botanical classification: *Dendranthema grandiflora* cultivar 'Golden Albany'.

Commercial classification: Decorative spray-type cut Chrysanthemum.

Parentage: Induced mutation of *Dendranthema grandiflora* cultivar 'Albany' (U.S. Plant Pat. No. 9,595).

Propagation:

*Type.*—Terminal tip cuttings.

*Time to rooting.*—Seven to ten days with soil temperatures of 21C.

*Rooting habit.*—Fine, fibrous and well-branched.

Plant description:

*Appearance.*—Perennial herbaceous decorative spray-type cut flower. Stems upright, uniform habit and freely branching.

*Flowering stem length.*—80 to 109 cm.

*Foliage description.*—Leaf arrangement: Alternate. Leaf size, fully expanded: Length: About 12 cm. Width: About 8 cm. Leaf apex: Acuminate. Leaf base: Attenuate. Leaf margin: Palmately lobed. Leaf texture: Abaxial and adaxial surfaces slightly pubescent. Veins prominent on abaxial surface. Color: Young foliage adaxial surface: 147A. Young foliage abaxial surface: 147B. Mature foliage adaxial surface: 147A. Mature foliage abaxial surface: 147B. Venation abaxial surface: 147B. Venation adaxial surface: 147B. Petiole: Length: About 3.5 cm. Color: 147A.

Flowering description:

*Appearance.*—Decorative inflorescence form. Inflorescences borne on terminals above foliage, arising from leaf axils. Disc and ray florets arranged acropetally on a capitulum.

*Flowering response.*—Under natural conditions, plant flower in the autumn/winter in the Northern Hemisphere. At other times of the year, inflorescence initiation and development can be induced under short day/long night conditions (at least 13.5 hours of darkness). Plants exposed to 1.5 to 2 weeks of long day/short night conditions after planting followed by photoinductive short day/long night conditions flower 55 to 60 days later.

*Postproduction longevity.*—In an interior environment, inflorescences of cut flowering stems will maintain good color and substance for at least three weeks in an interior environment following one week of cold storage.

*Quantity of inflorescences.*—About 15 inflorescences per flowering stem.

*Inflorescence size.*—Diameter: About 8 cm. Depth (height): About 3 cm. Diameter of disc: About 2.5 mm. Diameter of receptacle: About 7.5 mm.

*Ray florets.*—Shape: Fused at base, incurved, concave in cross-section, elongated, narrow. Size: Length: About 4.5 cm. Width: About 1.2 cm. Apex: Acute. Base: Attenuate. Margin: Entire. Texture: Satiny, smooth, glabrous, ribbed lengthwise. Aspect: Outwardly upright, outside florets are positioned about 45° to the base of the capitulum. Number of ray florets per inflorescence: About 307. Color: Immature: Adaxial surface: 5A. Abaxial surface: 5B. Mature: Adaxial surface: 9A, color does not fade with further development. Abaxial surface: 9A/9B, color does not fade with further development.

*Disc florets.*—Shape: Tubular. Size: Length: About 4.5 mm. Width: About 1 mm. Number of disc florets per inflorescence: About 9. Color: Immature: 154B. Mature: 3A.

*Peduncle.*—Aspect: Strong and angled about 35° to the stem. Length: First peduncle: About 7.5 cm. Fourth peduncle: About 13 cm. Seventh peduncle: About 18 cm. Texture: Glabrous. Color: 147B.

*Reproductive organs.*—Androecium: Present on disc florets only. Anther color: 3A. Pollen: Moderate, 3A in color. Gynoecium: Present on both ray and disc florets.

Disease resistance: No known Chrysanthemum diseases observed to date on plants grown under commercial greenhouse conditions.

Seed production: Seed production has not been observed.

It is claimed:

1. A new and distinct cultivar of Chrysanthemum plant named 'Golden Albany', as illustrated and described.

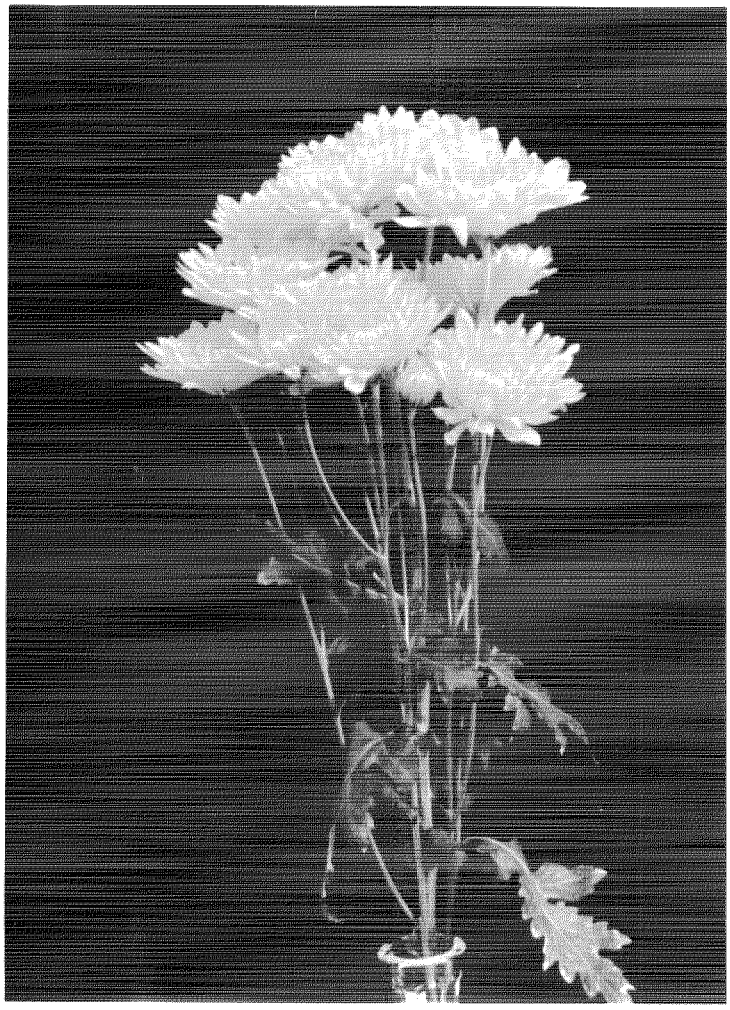

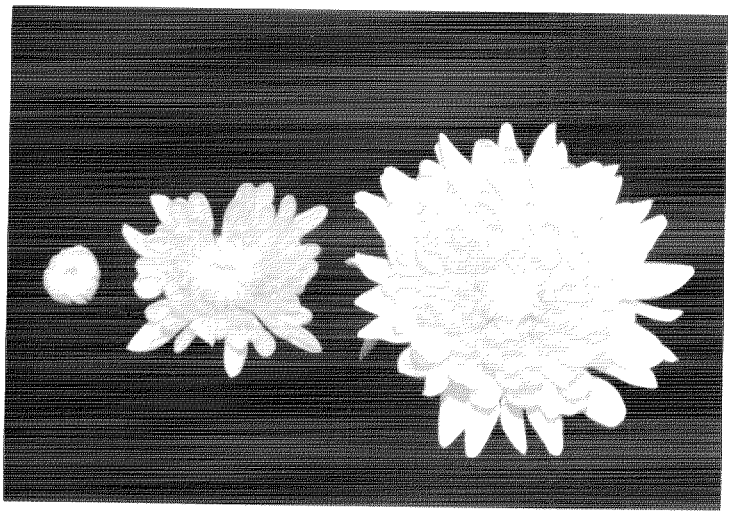

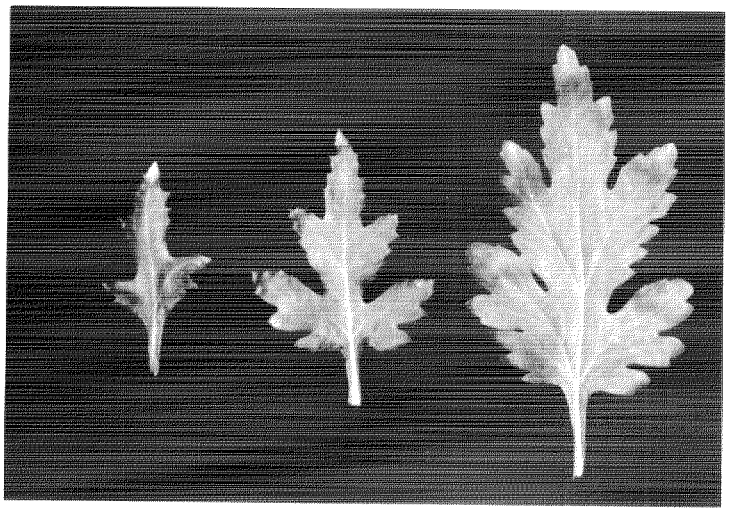

* * * * *